(12) United States Patent
Han et al.

(10) Patent No.: US 11,520,154 B2
(45) Date of Patent: Dec. 6, 2022

(54) ARTIFICIAL RETINA SYSTEM BASED ON AUGMENTED REALITY

(71) Applicant: CELLICO Inc., Seongnam-si (KR)

(72) Inventors: Eui Don Han, Seongnam-si (KR); Lee Woon Jang, Seongnam-si (KR)

(73) Assignee: CELLICO Inc., Seongnam-si (KR)

( * ) Notice: Subject to any disclaimer, the term of this patent is extended or adjusted under 35 U.S.C. 154(b) by 0 days.

(21) Appl. No.: 17/650,587

(22) Filed: Feb. 10, 2022

(65) Prior Publication Data
US 2022/0269087 A1  Aug. 25, 2022

(30) Foreign Application Priority Data

Feb. 24, 2021  (KR) .................. 10-2021-0024499

(51) Int. Cl.
| | |
|---|---|
| *G02B 27/01* | (2006.01) |
| *H04W 4/029* | (2018.01) |
| *A61F 2/14* | (2006.01) |
| *G02B 27/00* | (2006.01) |

(52) U.S. Cl.
CPC ............ *G02B 27/0172* (2013.01); *A61F 2/14* (2013.01); *G02B 27/0093* (2013.01); *H04W 4/029* (2018.02); *G02B 2027/014* (2013.01); *G02B 2027/0138* (2013.01); *G02B 2027/0178* (2013.01)

(58) Field of Classification Search
CPC ...... H04W 4/029; A61F 2/14; G02B 27/0172; G02B 27/017; G02B 27/0093; G02B 2027/0138; G02B 2027/014
USPC ........................................................ 359/630
See application file for complete search history.

(56) References Cited

U.S. PATENT DOCUMENTS

| | | | | |
|---|---|---|---|---|
| 9,192,464 | B2* | 11/2015 | Liran ................. | A61N 1/36046 |
| 2014/0031931 | A1* | 1/2014 | Liran ....................... | A61F 2/14 |
| | | | | 623/6.63 |
| 2015/0306379 | A1* | 10/2015 | Kokelmann ....... | A61N 1/36125 |
| | | | | 607/115 |

(Continued)

FOREIGN PATENT DOCUMENTS

| | | |
|---|---|---|
| JP | 4310247 B2 | 8/2009 |
| KR | 10-2013-0139280 A | 12/2013 |

(Continued)

OTHER PUBLICATIONS

Decision of Patent Grant for Korean Patent Application No. 10-2021-0024499, dated Nov. 18, 2021, Korean Intellectual Property Office. English translation.

(Continued)

*Primary Examiner* — William R Alexander
(74) *Attorney, Agent, or Firm* — ArentFox Schiff LLP

(57) ABSTRACT

An artificial retina system based on an augmented reality according to an embodiment of the present disclosure may include an external device and an artificial retina device. The external device may be disposed outside the human body, and may include a micro display providing a processed image which is image-processed based on external image information obtained by capturing an external region of a human body; and the artificial retina device may be disposed in an eyeball inside the human body, and may provide a retinal tissue included in the human body with an electrical signal corresponding to the processed image provided by the micro display.

12 Claims, 6 Drawing Sheets

(56) References Cited

U.S. PATENT DOCUMENTS

| | | | |
|---|---|---|---|
| 2016/0135988 A1* | 5/2016 | Gefen | A61F 2/1624 |
| | | | 606/4 |
| 2016/0317811 A1 | 11/2016 | Greenberg et al. | |
| 2017/0068119 A1* | 3/2017 | Antaki | G09B 21/008 |
| 2017/0224998 A1* | 8/2017 | Gefen | A61F 9/00 |
| 2019/0022376 A1* | 1/2019 | Zeck | A61N 1/0543 |
| 2019/0083776 A1* | 3/2019 | Rousseau | H01B 13/0036 |
| 2019/0209833 A1* | 7/2019 | Kim | A61N 1/36185 |

FOREIGN PATENT DOCUMENTS

| | | |
|---|---|---|
| KR | 10-2018-0121127 A | 11/2018 |
| KR | 10-2019-0107267 A | 9/2019 |
| KR | 102332169 B1 | 12/2021 |

OTHER PUBLICATIONS

Office action prior to the Decision of Patent Grant for Korean Patent Application No. 10-2021-0024499, dated Oct. 22, 2021, Korean Intellectual Property Office, English translation in its entirety included.

Second Office action for Korean Patent Application No. 10-2021-0024499, dated Sep. 17, 2021, Korean Intellectual Property Office, English translation in its entirety included.

First Office action for Korean Patent Application No. 10-2021-0024499, dated May 10, 2021, Korean Intellectual Property Office, English translation in its entirety included.

* cited by examiner

210

ARTIFICIAL RETINA SYSTEM BASED ON AUGMENTED REALITY

CROSS-REFERENCE TO RELATED APPLICATION(S)

This application claims benefit of priority to Korean Patent Application No. 10-2021-0024499 filed Feb. 24, 2021, in the Korean Intellectual Property Office, the contents of which is incorporated herein by reference in its entirety.

FIELD OF THE INVENTION

The present disclosure relates to an artificial retina system based on an augmented reality.

BACKGROUND OF THE INVENTION

In a conventional artificial retina device, a technique has been developed in which various image processing functions are added to a stimulation chip inserted under a retina. However, when using this conventional method, it is difficult to implement a high-resolution stimulation pixel due to an area of the chip, and power consumption may also be increased. Recently, various studies have been conducted to solve these problems.

RELATED ART DOCUMENT

Patent Document

Korean Patent No. 10-2157955 (registered on Sep. 14, 2020)

SUMMARY OF THE INVENTION

An aspect of the present disclosure may provide an artificial retina system based on an augmented reality, in which the artificial retina system may not only implement a high resolution without increasing a size of an artificial retina device but also reduce power consumption, by transmitting a processed image, which is image-processed based on external image information, to the artificial retina device disposed in an eyeball inside a human body by using a micro display of an external device disposed outside the human body.

Another aspect of the present disclosure may provide an artificial retina system based on an augmented reality, in which the artificial retina system may not require time to process an image, thus responding immediately to irradiated light, may increase reliability of an artificial retina chip by simplifying a structure of the chip, and may not need to transmit data at a high speed for processing an image, thus simplifying structures of wireless power and a data receiving end to be made smaller, by transmitting a processed image, which is image-processed based on external image information, to the artificial retina device disposed in an eyeball inside a human body by using a micro display of an external device disposed outside the human body.

According to an aspect of the present disclosure, an artificial retina system based on an augmented reality may include an external device and an artificial retina device. The external device may be disposed outside the human body, and may include a micro display providing a processed image which is image-processed based on external image information obtained by capturing an external region of a human body; and the artificial retina device may be disposed in an eyeball inside the human body, and may provide a retinal tissue included in the human body with an electrical signal corresponding to the processed image provided by the micro display.

The external device may include a camera, an image processor and a micro display. The camera may provide the external image information by capturing the external region, the image processor may provide the processed image by image-processing the external image information, and the micro display may display the processed image on the micro display.

The external device may further include a digital controller providing a first control signal controlling the image processor and a second control signal controlling the artificial retina device.

The digital controller may select one of a plurality of algorithms for image-processing the external image information, based on the first control signal.

The digital controller may wirelessly provide the artificial retina device with power or data information, based on the second control signal.

The artificial retina device may control the pulse width or pulse period of the electrical signal, based on the data information.

The artificial retina device may selectively control some of pixels included in the artificial retina device, based on the data information.

The external device may have a shape of a pair of sunglasses, and the micro display may be disposed on an inner surface of a lens region included in the pair of sunglasses. Alternatively, a small projector instead of the micro display may be disposed on the inner surface of the lens region to transmit the processed image. Alternatively, the processed image may be transmitted into a human eye by adjusting a focal length through mirror reflection and glass refraction.

The pair of sunglasses may further include a body-mounted battery providing the external device with the power.

The pair of sunglasses may further include a speaker providing a sound notification by converting the external image information into a sound signal.

The pair of sunglasses may provide a navigation service by being linked to a smartphone, based on the external image information.

The pair of sunglasses may further include a sunshade blocking external light from being transmitted between the external device and a face included in the human body.

The artificial retina system based on an augmented reality may select one of the plurality of algorithms, based on the first control signal during a first time interval, and may provide the data information, based on the second control signal during a second time interval after the first time interval.

The artificial retina system may be set to be optimized for the user, based on the first control signal provided during the first time interval and the second control signal provided during the second time interval.

In addition to the above-mentioned technical tasks of the present disclosure, other features and advantages of the present disclosure may be described below, or may be clearly understood by those skilled in the art to which the present disclosure pertains from such description and explanation.

DETAILED DESCRIPTION OF THE INVENTION

Figure 1:
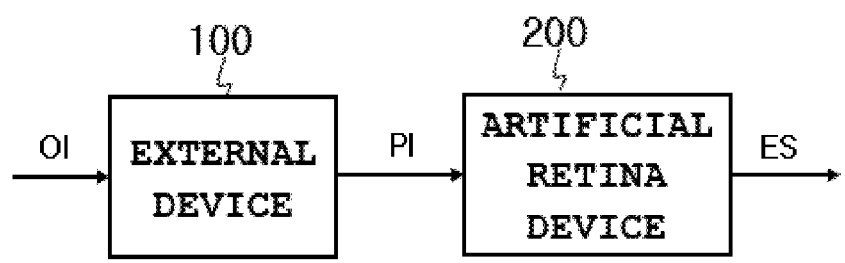
FIG. 1 is a view showing an artificial retina system based on an augmented reality according to embodiments of the present disclosure.

In the specification, in adding reference numerals to components throughout the drawings, it is to be noted that like reference numerals designate like components even though components are shown in different drawings.

Meanwhile, meanings of the terms described in this specification should be understood as follows.

Singular forms used herein are intended to include plural forms unless explicitly indicated otherwise, and a scope of the present disclosure is not limited by the terms used herein.

It is to be understood that a term "include" or "have" does not preclude the presence or addition of one or more other features, numerals, operations, components, parts or combinations thereof, which is mentioned in the specification.

Hereinafter, embodiments of the present disclosure are described in detail with reference to the accompanying drawings.

Figure 2:
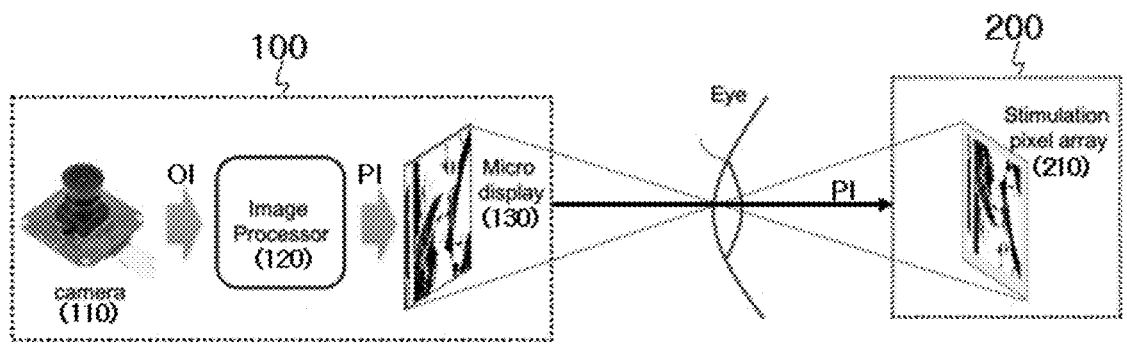
FIG. 2 is a view showing an example of the artificial retina system based on an augmented reality of FIG. 1.

FIG. 1 is a view showing an artificial retina system based on an augmented reality according to embodiments of the present disclosure; FIG. 2 is a view showing an example of the artificial retina system based on an augmented reality of FIG. 1; and FIG. 3 is a view showing a digital controller included in the artificial retina system based on an augmented reality of FIG. 1.

Figure 3:
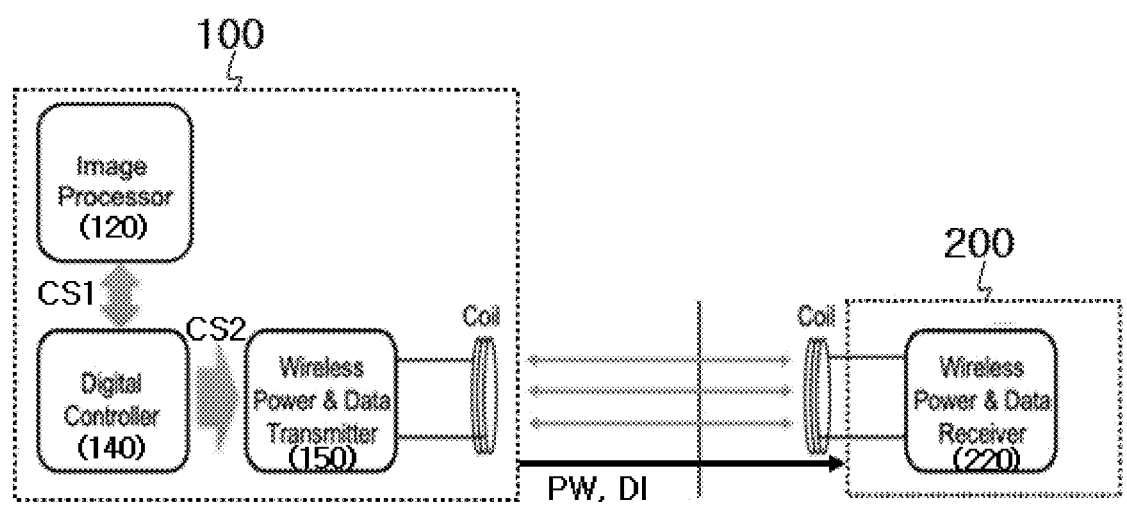
FIG. 3 is a view showing a digital controller included in the artificial retina system based on an augmented reality of FIG. 1.

Referring to FIGS. 1 to 3, an artificial retina system 10 based on an augmented reality according to an embodiment of the present disclosure may include an external device 100 and an artificial retina device 200. The external device 100 may include a micro display 130 providing a processed image PI which is image-processed based on external image information OI obtained by capturing an external region OR of a human body. For example, the external device 100 may include a camera 110, an image processor 120 and the micro display 130. The camera 110 may provide the external image information OI by capturing the external region OR, and the image processor 120 may provide the processed image PI by image-processing the external image information 01. In addition, the micro display 130 may display the processed image PI on the micro display 130.

The external device 100 may be disposed outside the human body. For example, the external device 100 may have a shape of a pair of sunglasses and used by being mounted on the nose and ears of the human body. In this case, the camera 110, the image processor 120 and the micro display 130 may be embedded in the pair of sunglasses. The micro display 130 may display the processed image PI which is image-processed. The processed image PI displayed on the micro display 130 disposed in a lens region LR of the pair of sunglasses may be transmitted to the artificial retina device 200, disposed in a retina of an eye, through an eye lens.

The artificial retina device 200 disposed in an eyeball inside the human body may provide a retinal tissue included in the human body with an electrical signal ES corresponding to the processed image PI provided by the micro display 130.

The artificial retina system 10 based on an augmented reality according to the present disclosure may not only implement a high resolution without increasing a size of the artificial retina device 200 but also reduce power consumption by transmitting the processed image, which is image-processed based on the external image information OI, to the artificial retina device 200 disposed in the eyeball inside the human body by using the micro display 130 of the external device 100 disposed outside the human body.

In an embodiment, the external device 100 may further include a digital controller 140 providing a first control signal CS1 controlling the image processor 120 and a second control signal CS2 controlling the artificial retina device 200.

In an embodiment, the digital controller 140 may select one of a plurality of algorithms for image-processing the external image information OI, based on the first control signal CS1. For example, the plurality of algorithms may be a first algorithm to a fourth algorithm. An edge enhancement technique may be applied to the first algorithm, a contrast enhancement technique may be applied to the second algorithm, and an inverse filtering technique may be applied to the third algorithm. In addition, a non-flicker vision technique may be applied to the fourth algorithm. A user using the artificial retina system 10 according to the present disclosure may receive, from the artificial retina device 200, the processed image PI which is image-processed according to the first to fourth algorithms, based on the first control signal CS1. In this case, the user may select an algorithm providing the user with an optimal image from the processed images PIs provided according to the first algorithm to the fourth algorithm.

FIGS. 4 to 7 are views each showing information data used in the artificial retina system based on an augmented reality of FIG. 1.

Referring to FIGS. 1 to 7, the artificial retina system 10 based on an augmented reality according to an embodiment of the present disclosure may include the external device 100 and the artificial retina device 200, and the external device 100 may further include the digital controller 140 providing the first control signal CS1 controlling the image processor 120 and the second control signal CS2 controlling the artificial retina device 200.

In an embodiment, the digital controller 140 may wirelessly provide the artificial retina device 200 with power PW or data information DI, based on the second control signal CS2. For example, when the artificial retina device 200 lacks the power, the digital controller 140 may wirelessly provide the artificial retina device 200 with the power PW of a battery included in the external device 100, based on the second control signal CS2.

In an embodiment, the artificial retina device 200 may control a pulse size of the electrical signal ES based on the data information DI. For example, the electrical signal ES provided by the artificial retina device 200 may be a first electrical signal ES1. A pulse size of the first electrical signal ES1 may be a first pulse size A1. In this case, the user using the artificial retina system 10 according to the present disclosure may set a pulse size providing the user with the optimal image by adjusting the pulse size of the electrical signal ES. The electrical signal ES whose pulse size is adjusted by the user may be a second electrical signal ES2, and a pulse size of the second electrical signal ES2 may be a second pulse size A2.

In an embodiment, the artificial retina device 200 may control a pulse width of the electrical signal ES, based on the data information DI. For example, the electrical signal ES provided by the artificial retina device 200 may be the first electrical signal ES1. The pulse width of the first electrical signal ES1 may be a first pulse width B1. In this case, the user using the artificial retina system 10 according to the present disclosure may set a pulse width providing the user with the optimal image by adjusting the pulse width of the electrical signal ES. The electrical signal ES whose pulse width is adjusted by the user may be a third electrical signal ES3, and a pulse width of the third electrical signal ES3 may be a second pulse width B2.

In an embodiment, the artificial retina device 200 may control a pulse period of the electrical signal ES, based on the data information DI. For example, the electrical signal ES provided by the artificial retina device 200 may be the first electrical signal ES1. A pulse size of the first electrical signal ES1 may be a first pulse period C1. In this case, the user using the artificial retina system 10 according to the present disclosure may set the pulse period providing the user with the optimal image by adjusting the pulse period of the electrical signal ES. The electrical signal ES whose pulse period is adjusted by the user may be a fourth electrical signal ES4, and a pulse period of the fourth electrical signal ES4 may be a second pulse period C2.

Figure 4:
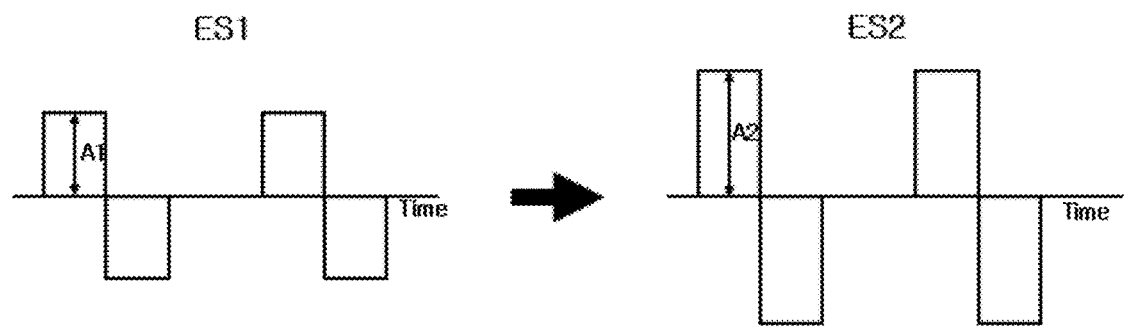
FIGS. 4 to 7 are views each showing information data used in the artificial retina system based on an augmented reality of FIG. 1.
Figure 5:
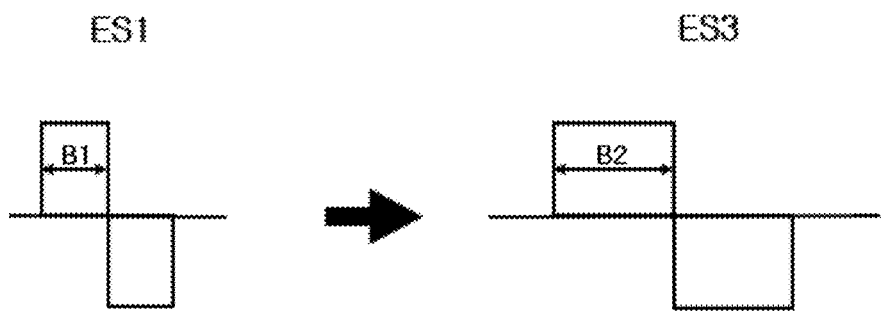
Figure 6:
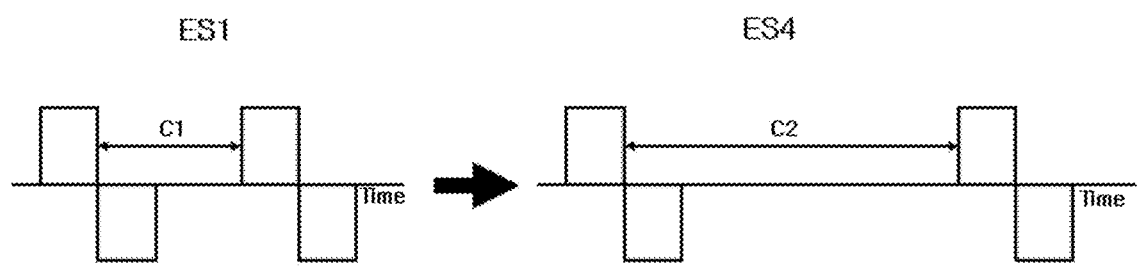
Figure 7:
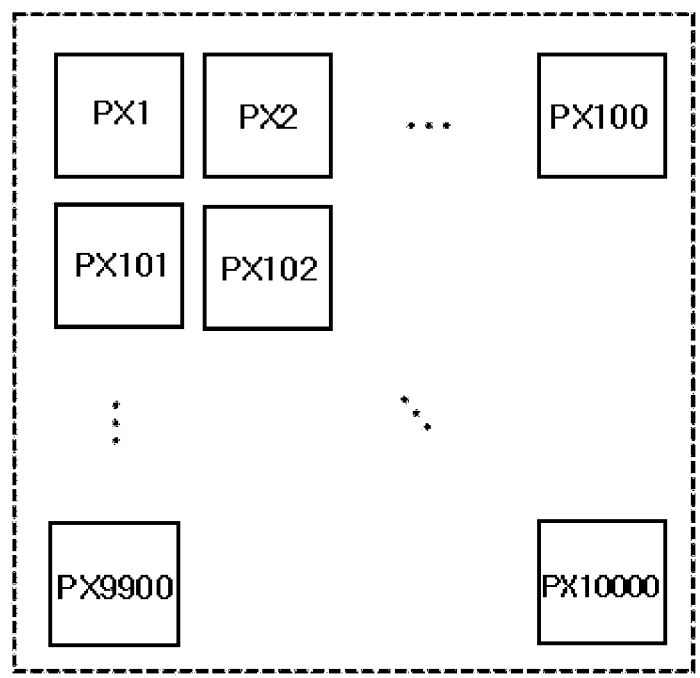

In more detail, the first pulse size A1 corresponding to the pulse size of the first electrical signal ES1 and the second pulse size A2 corresponding to the pulse size of the second electrical signal ES2, in FIGS. 4 to 6, may each be proportional to a light intensity of the display. In addition, the first pulse width B1 corresponding to the pulse width of the first electrical signal ES1 and the second pulse width B2 corresponding to the pulse width of the third electrical signal ES3 may be controlled based on the wireless data information DI, and the first pulse period C1 corresponding to the pulse period of the first electrical signal ES1 and the second pulse period C2 corresponding to the pulse period of the fourth electrical signal ES4 may also each be controlled based on the wireless data information DI.

In an embodiment, the artificial retina device 200 may selectively control some of the pixels included in the artificial retina device 200, based on the data information DI. For example, the artificial retina device 200 may include a simulation pixel array 210 and the simulation pixel array may include a plurality of pixels. The simulation pixel array 210 may include a first pixel PX1 to a 10000th pixel PX10000. In this case, the artificial retina device 200 may turn on even-numbered pixels among the pixels based on first data information DI1 and control the same. In addition, the artificial retina device 200 may turn on odd-numbered pixels among the pixels based on second data information DI2 and control the same. Here, the description describes a method of selectively controlling the odd-numbered and even-numbered pixels. However, the simulation pixel array 210 included in the artificial retina device 200 may be controlled by various methods.

Figure 8:
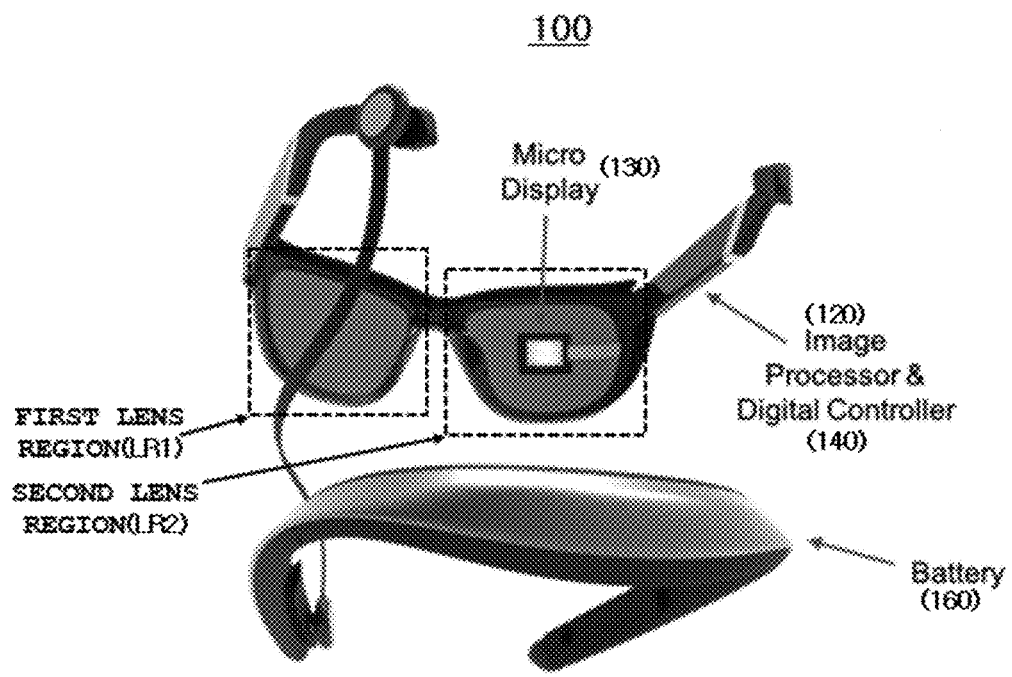
FIGS. 8 and 9 are views each showing an example in which the artificial retina system based on an augmented reality of FIG. 1 has a shape of a pair of sunglasses.
Figure 9:
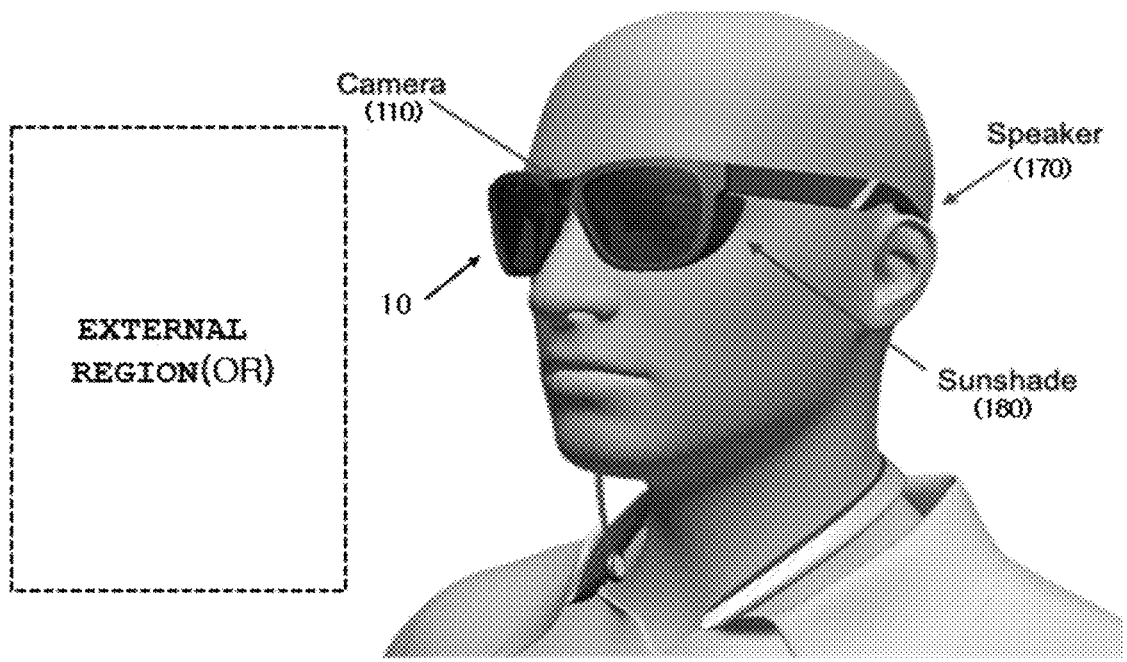
Figure 10:
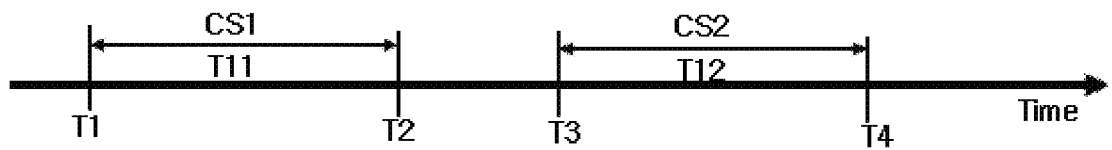
FIG. 10 is a view showing an operation example of the artificial retina system based on an augmented reality of FIG. 1.

FIGS. 8 and 9 are views each showing an example in which the artificial retina system based on an augmented reality of FIG. 1 has the shape of the pair of sunglasses; and FIG. 10 is a view showing an operation example of the artificial retina system based on an augmented reality of FIG. 1.

Referring to FIGS. 1 to 10, the artificial retina system 10 based on an augmented reality according to an embodiment of the present disclosure may include the external device 100 and the artificial retina device 200. The external device 100 may include the camera 110, the image processor 120 and the micro display 130.

In an embodiment, the external device 100 may have a shape of the pair of sunglasses, and the micro display 130 may be disposed on an inner surface of the lens region LR included in the pair of sunglasses. Alternatively, a small projector instead of the micro display 130 may be disposed on the inner surface of the lens region LR to transmit the processed image PI into the eye. Alternatively, the processed image PI may be transmitted into the eye by adjusting a focal length through mirror reflection and glass refraction. For example, the lens region LR may include a first lens region LR1 and a second lens region LR2. The camera 110 may be disposed on a center of a portion where the first lens region LR1 and the second lens region LR2 are connected to each other. The micro display 130 may be disposed on the inner surface of the first lens region LR1 or that of the second lens region LR2. The inner surface may be a surface opposite to a surface facing the external region OR in the lens region LR.

In an embodiment, the pair of sunglasses may further include a body-mounted battery 160 providing the external device 100 with the power PW. For example, the body-mounted battery 160 may be mounted on a neck of the human body.

In an embodiment, the pair of sunglasses may further include a speaker 170 providing a sound notification by converting the external image information OI into a sound signal into a sound signal. For example, the user using the artificial retina system 10 according to the present disclosure may not be able to accurately identify the external image information OI due to a visual problem. In this case, when a factor dangerous to the user is detected as a result of processing the image based on the external image information OI, the sound notification may be provided as a sound signal to the user using the artificial retina system 10 according to the present disclosure. The speaker 170 providing the sound notification may be disposed on a leg of the pair of sunglasses. In this case, the speaker 170 may be a bone conduction speaker. In addition, the pair of sunglasses may provide a navigation service by being linked to a smartphone, based on the external image information OI. For example, the user using the pair of sunglasses according to the present disclosure may receive a voice guidance service through the speaker 170 included in the pair of sunglasses linked to the smartphone.

In an embodiment, the pair of sunglasses may further include a sunshade 180 blocking external light from being transmitted between the external device 100 and a face included in the human body. For example, if the external light passes through a gap between the pair of sunglasses and the face, the user using the artificial retina system according to the present disclosure may have a problem in recognizing the processed image PI. To prevent this problem, the sunshade 180 may be used to block the gap between the pair of sunglasses and the face.

In an embodiment, the artificial retina system 10 based on an augmented reality may select one of the plurality of algorithms, based on the first control signal CS1 during a first time interval TI1, and may provide the data information DI, based on the second control signal CS2 during a second time interval TI2 after the first time interval TI1. For example, the first time interval TI1 may be a time interval from a first time T1 to a second time T2, and the second time interval TI2 may be a time interval from a third time T3 to a fourth time T4. The plurality of algorithms may be the first algorithm to the fourth algorithm, and the user using the artificial retina system 10 according to the present disclosure may primarily select the optimal algorithm suitable for the user from the first to fourth algorithms, based on the first control signal CS1 during the first time interval TI1. The user may then provide the artificial retina device 200 with the data information DI, based on the second control signal CS2 during the second time interval TI2, and thus control the pulse size, pulse width and pulse period of the electrical signal ES, thereby secondarily selecting an optimal set value of the electrical signal ES, which is suitable for the user. In an embodiment, the artificial retina system 10 may be set to be optimized for the user, based on the first control signal CS1 provided during the first time interval TI1 and the second control signal CS2 provided during the second time interval TI2.

The artificial retina system 10 based on an augmented reality according to the present disclosure may not only implement the high resolution without increasing the size of the artificial retina device 200 but also reduce the power consumption, by transmitting the processed image PI, which is image-processed based on the external image information OI, to the artificial retina device disposed in the eyeball inside the human body by using the micro display 130 of the external device 100 disposed outside the human body.

In addition, the artificial retina system 10 based on an augmented reality according to the present disclosure may not require time to process the image in the artificial retina device 200, thus responding immediately to irradiated light, may increase reliability of an artificial retina chip by simplifying a structure of the chip, and may not need to transmit the data at a high speed for processing the image, thus simplifying structures of the wireless power and a data receiving end to be made smaller, by transmitting the processed image PI, which is image-processed based on the external image information OI, to the artificial retina device 200 disposed in the eyeball inside the human body by using the micro display 130 of the external device disposed outside the human body.

As set forth above, the present disclosure as described above may provide the following effects.

The artificial retina system based on an augmented reality according to the present disclosure may not only implement the high resolution without increasing the size of the artificial retina device but also reduce the power consumption by transmitting the processed image, which is image-processed based on the external image information, to the artificial retina device disposed in the eyeball inside the human body by using the micro display of the external device disposed outside the human body.

The artificial retina system based on an augmented reality according to the present disclosure may not require the time to process the image, thus responding immediately to the irradiated light, may increase the reliability of the artificial retina chip by simplifying the structure of the chip, and may not need to transmit the data at the high speed for processing the image, thus simplifying the structures of the wireless power and the data receiving end to be made smaller, by transmitting the processed image, which is image-processed based on the external image information, to the artificial retina device disposed in the eyeball inside the human body by using the micro display of the external device disposed outside the human body.

What is claimed is:

1. An artificial retina system based on an augmented reality, the system comprising:
    an external device disposed outside the human body, and including a micro display providing a processed image which is image-processed based on external image information obtained by capturing an external region of a human body; and
    an artificial retina device disposed in an eyeball inside the human body, and providing a retinal tissue included in the human body with an electrical signal corresponding to the processed image provided by the micro display,
    wherein the external device further includes a digital controller providing a first control signal controlling the image processor and a second control signal controlling the artificial retina device,
    wherein the digital controller wirelessly provides the artificial retina device with power or data information, based on the second control signal,
    wherein the artificial retina device controls the pulse width or pulse period of the electrical signal, based on the data information,
    wherein the artificial retina device selectively controls some of pixels included in the artificial retina device, based on the data information.

2. The system of claim 1, wherein the external device includes
    a camera providing the external image information by capturing the external region,
    an image processor providing the processed image by image-processing the external image information, and
    the micro display displaying the processed image on the micro display.

3. The system of claim 2, wherein the digital controller selects one of a plurality of algorithms for image-processing the external image information, based on the first control signal.

4. The system of claim 1, wherein the external device has a shape of a pair of sunglasses, and the micro display is disposed on an inner surface of a lens region included in the pair of sunglasses.

5. The system of claim 4, wherein the pair of sunglasses further includes a body-mounted battery providing the external device with the power.

6. The system of claim 5, wherein the pair of sunglasses further includes a speaker providing a sound notification by converting the external image information into a sound signal.

7. The system of claim 6, wherein the pair of sunglasses further includes a sunshade blocking external light from being transmitted between the external device and a face included in the human body.

8. The system of claim 7, wherein the artificial retina system based on an augmented reality selects one of the plurality of algorithms, based on the first control signal during a first time interval, and provides the data information, based on the second control signal during a second time interval after the first time interval.

9. The system of claim 8, wherein the artificial retina system is set to be optimized for the user, based on the first control signal provided during the first time interval and the second control signal provided during the second time interval.

10. The system of claim 4, wherein a small projector instead of the micro display is disposed on the inner surface of the lens region to transmit the processed image.

11. The system of claim 4, wherein the processed image is transmitted into a human eye by adjusting a focal length through mirror reflection and glass refraction.

12. The system of claim 6, wherein the pair of sunglasses provides a navigation service by being linked to a smartphone, based on the external image information.

* * * * *